United States Patent
Ditscher et al.

(10) Patent No.: US 10,413,223 B2
(45) Date of Patent: Sep. 17, 2019

(54) DIAGNOSTIC TAPE UNIT AND A PROCESS FOR ITS PRODUCTION

(75) Inventors: Wolfgang Ditscher, Kaiserslautern (DE); Karlheinz Joest, Wald-Michelbach (DE); Ria Daumbach, Mannheim (DE); Alexander Kasejew, Mannheim (DE); Daniel Aigl, Edingen-Neckarhausen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 257 days.

(21) Appl. No.: 12/408,396

(22) Filed: Mar. 20, 2009

(65) Prior Publication Data
US 2009/0238721 A1    Sep. 24, 2009

(30) Foreign Application Priority Data
Mar. 20, 2008  (EP) .................................... 08153092

(51) Int. Cl.
*G01N 33/487*   (2006.01)
*A61B 5/15*     (2006.01)
*A61B 5/151*    (2006.01)

(52) U.S. Cl.
CPC ............ *A61B 5/1411* (2013.01); *A61B 5/151* (2013.01); *A61B 5/150022* (2013.01); *A61B 5/150274* (2013.01); *A61B 5/150358* (2013.01); *G01N 33/48764* (2013.01); *A61B 5/150282* (2013.01); *A61B 2562/0295* (2013.01)

(58) Field of Classification Search
CPC ................................................. G01N 33/48764
See application file for complete search history.

(56) References Cited

U.S. PATENT DOCUMENTS

| | | | | |
|---|---|---|---|---|
| 3,654,035 | A | * | 4/1972 | Takimoto ...................... 156/505 |
| 4,061,286 | A | * | 12/1977 | King et al. ................. 242/523.1 |
| 4,062,719 | A | | 12/1977 | Masuzima et al. |
| 4,218,421 | A | * | 8/1980 | Mack et al. .................... 422/66 |
| 4,844,370 | A | | 7/1989 | Sakaguchi et al. |
| 4,853,059 | A | * | 8/1989 | Meguro .................. B01L 3/505 |
| | | | | 156/157 |

(Continued)

FOREIGN PATENT DOCUMENTS

| | | |
|---|---|---|
| DE | 19849539 A1 | 5/2000 |
| EP | 0299517 B1 | 10/1993 |

(Continued)

OTHER PUBLICATIONS

Bruno Lotter, Manufacturing Assembly Handbook, 1989, ISBN 0-408-03561-7, pp. 269-272, Buttersworths.

(Continued)

*Primary Examiner* — Jill A Warden
*Assistant Examiner* — Brittany I Fisher

(57) ABSTRACT

A diagnostic tape unit and a process for producing it are provided, in which disposable, test units are applied to a rollable transport tape which is wound onto an unwinding spool and is connected to a take-up spool such that the test units can be successively made available to a user by winding on the transport tape. One or both of the leading end and trailing end of the transport tape is connected to their corresponding spools by means of an auxiliary tape.

22 Claims, 1 Drawing Sheet

(56) References Cited

U.S. PATENT DOCUMENTS

| | | | |
|---|---|---|---|
| 4,899,245 A | | 2/1990 | Kubota |
| 4,947,277 A | | 8/1990 | Kubota |
| 5,077,010 A | * | 12/1991 | Ishizaka et al. .............. 422/408 |
| 5,280,862 A | | 1/1994 | Oya et al. |
| 8,226,793 B2 | | 7/2012 | Zimmer et al. |
| 2005/0245845 A1 | | 11/2005 | Roe et al. |
| 2006/0163405 A1 | | 7/2006 | Nishiwaki |
| 2007/0038150 A1 | | 2/2007 | Calasso et al. |
| 2011/0243810 A1 | * | 10/2011 | Schosnig ......... G01N 33/48764 422/400 |

FOREIGN PATENT DOCUMENTS

| | | |
|---|---|---|
| EP | 0974964 B1 | 12/2004 |
| EP | 1593424 A1 | 11/2005 |
| JP | 04-243755 A | 8/1992 |
| JP | 05334843 A | 12/1993 |
| JP | 10208434 A | 8/1998 |
| JP | 10-255260 A | 9/1998 |
| JP | 2007-535351 A | 12/2007 |
| WO | 2007/077212 A2 | 7/2007 |

OTHER PUBLICATIONS

Text of First Office Action in China, Application No. 2009101277754, 11 pages no date provided.

\* cited by examiner

DIAGNOSTIC TAPE UNIT AND A PROCESS FOR ITS PRODUCTION

CLAIM OF PRIORITY

The present application is a continuation application based on and claiming, priority to European Patent Application No. 08 153 092.5, filed Mar. 20, 2008, which is hereby incorporated by reference in its entirety.

TECHNICAL FIELD OF THE INVENTION

The present application relates to a product and process for producing a diagnostic tape unit comprising disposable test units, and more particularly to such a tape unit in which a transport tape carrying disposable test units is wound onto an unwinding spool and is connected to a take-up spool such that the test units can be successively made available to a user by winding on the transport tape.

BACKGROUND

Diagnostic tape units have been designed typically for blood sugar tests in order to further improve the user-friendliness compared to the test strip systems that are on the market. In order to simplify the handling of disposable test units, a large number of such test units can be compactly stored on a transport tape that can be rolled up and also disposed of again by the tape transport. It is possible to provide such a tape unit in the form of a consumable cassette for use in a hand-held device in order to provide the user with self-tests which proceed substantially automatically. For example, previous publications such as WO 2005/104948 describe simplified integration of disposable test units on a carrier tape.

The object of the invention is to further develop the methods and products known in the prior art and to specify an optimized construction also with regard to mass production for a tape unit of the type stated above that functions reliably.

SUMMARY

This object and others that will be appreciated by a person of ordinary skill in the art have been achieved according to the embodiments of the present invention disclosed herein. In one embodiment, the present invention comprises a process in which the leading end of the transport tape is connected to the take-up spool by means of an auxiliary tape, and/or the trailing end of the transport tape is connected to the unwinding spool by means of an auxiliary tape. This simplifies the attachment of the tape to the spools and does not have to be integrated into the process of winding the test tape or material. In particular it is also unnecessary to wind on any more material than is required for the tests. Thus, the last test unit can also be used without difficulty without the transport tape losing its tension and becoming detached from the unwinding spool. A special arrangement of the transport tape, e.g. with regard to test element distribution along the tape, can also be avoided as a result of using the auxiliary tape. Furthermore, the auxiliary tape can be optimized for the spool connection especially in short cycle times and can be used in subsequent production steps, for example to check the torque on the spools without using test tape for this purpose.

In a further embodiment, the present invention relates to a process in which the take-up spool and the unwinding spool are firstly connected by the auxiliary tape and that then the auxiliary tape is severed between the spools to form a leader tape and trailer tape and is connected to the tape ends of the transport tape. In order to create a simple tape join without an open adhesive gap, the transport tape can be butt joined to the auxiliary tape by means of a piece of adhesive tape. Alternatively it is also possible to join the transport tape to the auxiliary tape in an overlapping manner. In this case the transport tape and the auxiliary tape are materially joined together, such as by being glued together in an overlapping region at their ends.

In yet a further embodiment, a free tape end section of the transport tape or of an auxiliary tape connected thereto is permanently connected to the unwinding spool and/or take-up spool by means of a material (integral) or frictional tape connection such that the tape end section does not self-detach when it unwinds. Such a method of connection allows the assembly to be further simplified and enables compact spools to be created without additional aids or parts.

A material tape connection can be made by welding or gluing. This can be particularly simply accomplished by using a hot-melt adhesive to make the integral tape connection. For this purpose the tape end section and/or the spool that is to be connected thereto can be coated as a connecting partner with a hot-melt adhesive in a preparatory step and subsequently the connecting partners can be joined together in a planar fashion by applying pressure and heat preferably by means of a welding die.

Another improvement provides that the hot-melt adhesive is applied in a wet form and subsequently dried so that a portion of solids remains as the adhesive layer. An adhesive layer with a layer thickness of less than 50 µm, preferably about 10 µm is preferably applied.

In other embodiments, the auxiliary tape is coated with hot-melt adhesive over its entire length, such as by means of a coextrusion process.

A sufficiently secure attachment is typically provided when the tape end section is firmly connected to the spool over a wrap region of less than 180°, preferably of less than 90°.

It is also conceivable that the frictional tape connection is made by a clamp connection between the tape end section and the associated spool. This further reduces the number of parts in that the tape end section is clamped in a clamping gap of the associated spool.

Another variant of the invention provides that the transport tape is formed from two transport tape sections joined at a connection site. Such a splice connection allows the specific structuring of sections of a test tape that is manufactured as an endless material. In this connection a part of the transport tape that has been registered as waste is cut out and subsequently the remaining transport tape sections are spliced together in a first step.

The transport tape sections can also be connected together at the connecting site by a piece of adhesive tape, and in one embodiment this is provided by the transport tape sections being butt joined at the connecting site.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
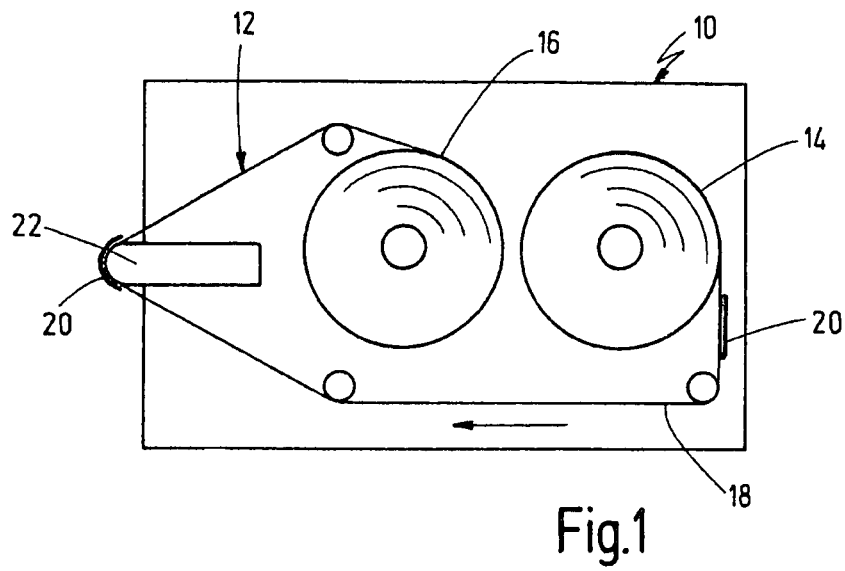
FIG. 1 shows a diagnostic tape unit in the form of a tape cassette in a simplified cross-section.

The diagnostic tape cassette 10 for carrying out blood sugar tests shown in FIG. 1 comprises a test tape 12, an unwinding spool 14 for unwinding unused test tape and a take-up spool 16 for winding used test tape, wherein the test tape 12 has a transport or carrier tape 18 that can be rolled up and a plurality of test units 20 stored or otherwise provided thereon for successive single uses. The test units 20 that are shown are provided as analytical test fields with a test chemistry for a glucose detection. As will be appreciated by persons of ordinary skill in the art, the test units 20 provided on the transport tape 18 may comprise lancing elements for a skin puncture (not shown) as an alternative or in addition to test units 20 comprising analytical test fields. The test tape 12 can be wound forwards by means of a rotary drive of the take-up spool 16 such that the test units 20 can be made available to the user at an application site 22. Such a tape cassette 10 can be used as a consumable for user self-tests in a hand-held device (not shown). Further details of such a use may be derived for example from the application EP-A 1 878 379, the disclosure of which is hereby incorporated herein by reference in its entirety.

Figure 2:
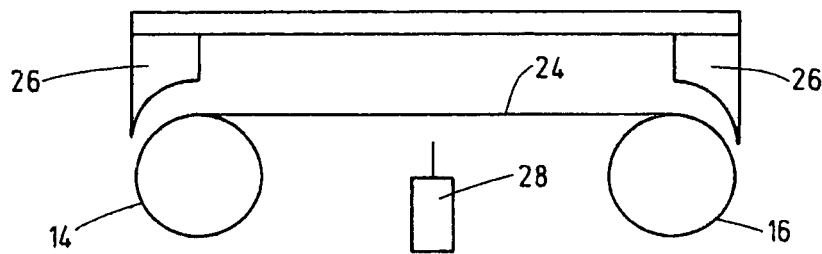
FIG. 2 shows a device for preassembling a tape unit according to FIG. 1.

FIG. 2 illustrates an embodiment for a production step for the preassembly of the tape cassette 10. In order to attach the tape, the tape ends of an auxiliary tape 24 are integrally connected to the take-up spool 14 and to the unwinding spool 16. This can be achieved in one embodiment by a hot-melt adhesive bond using welding dies 26 which can be pressed against respective segments of the spools in order to activate the hot-melt adhesive. Then the auxiliary tape 24 is severed by a cutting device 28 in order to splice on a desired length of transport tape 18 provided with the test units 20.

Figure 3:
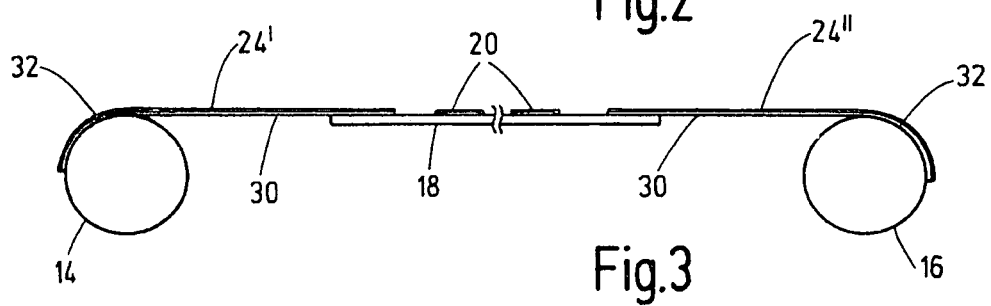
FIGS. 3 and 4 show different embodiments of a tape arrangement of the tape unit with adhesive tape holding means to connect it to the winding spools.

In the embodiment shown in FIG. 3, the auxiliary tape 24 is coated with a layer of hot-melt adhesive 30. In one embodiment, a hot-melt adhesive is applied as a liquid to one side of the auxiliary tape 24 by a coextrusion process during the production of the auxiliary tape, and is dried such that a portion of solid remains as a hot-melt adhesive layer 30 having a layer thickness of about 10 µm. A connection 32 is then made on the spools 14, 16 in the subsequent gluing by means of the welding die 26 which secures the auxiliary tape 24 against self-detachment.

In a subsequent manufacturing step the auxiliary tape divided into a trailer tape 24' connected to the unwinding spool 14 and a leader tape 24" connected to the take-up spool 16 is connected to the transport tape 18. In this regard, the transport tape 18 can be cut to a suitable length from an endless material and spliced in, in order to provide a desired number of test units 20. For this purpose the free tape ends are joined in an overlapping manner and permanently glued together in the overlapping area by activating the hot-melt adhesive layer 30. In the unused state, the tape material 12 is wound onto the take-up spool 14 in the cassette 10 and the leader tape 24" is pulled through until the first test unit 20 is made available.

Figure 4:
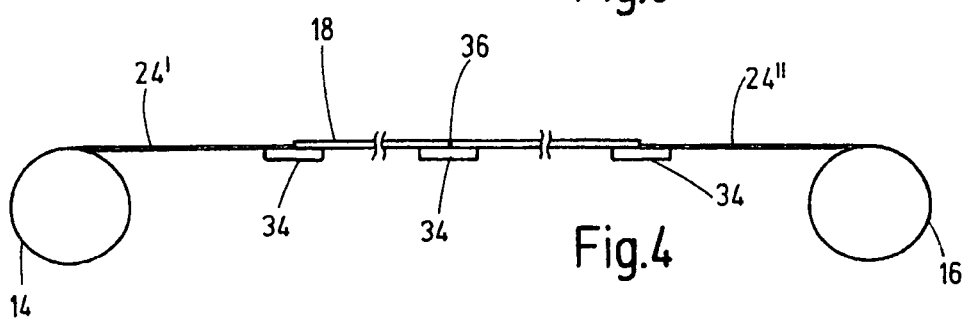

FIG. 4 shows a further embodiment in which a tape connection is made by special pieces of adhesive tape 34. In this case the trailer tape 24' and the leader tape 24" are butt joined without overlap and the pieces of adhesive tape 34 absorb the tensile loads that occur during use.

Such an adhesive tape connection can also be used to remove defective material from the test tape 12. For this purpose the test units 20 are examined for rejects and a corresponding part of the transport tape 18 is cut out. Then the remaining sections of the transport tape can be joined together again at a connecting site by means of a piece of adhesive tape 34.

In various other embodiments, the auxiliary tape 24 can also be connected to the spools 14, 16 free of adhesive for example by ultrasonic welding or by a clamp connection where the ends of the tape is held in a frictional manner, such as in a clamping gap (not shown) of the relevant spool.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, of other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A method for assembling a diagnostic tape unit comprising a plurality of disposable test units provided on a rollable tape such that the test units can be successively made available to a user by winding of the rollable tape, the method comprising the steps of:
   integrally connecting a take-up spool and an unwinding spool of the diagnostic tape unit by an auxiliary tape, wherein no disposable test units are on the auxiliary tape, which is structured only for a tape connection of the rollable tape to the take-up and unwinding spools;
   severing the auxiliary tape to form a leader tape extending from the take-up spool and a trailer tape extending from the unwinding spool;

connecting a leading end of a transport tape of the rollable tape including the plurality of disposable test units to the take-up spool using the leader tape extending from the take-up spool, wherein the leader tape and the transport tape are separate from one another before connecting the leading end of the transport tape to the take-up spool and are joined to one another to connect the leading end of the transport tape to the take-up spool;

connecting a trailing end of the transport tape to the unwinding spool using the trailer tape extending from the unwinding spool so that the disposable test units of the rollable tape are provided on the transport tape and no disposable test units are on the trailer tape, wherein the trailer tape and the transport tape are separate from one another before connecting the trailing end of the transport tape to the unwinding spool and are joined to one another to connect the trailing end of the transport tape to the unwinding spool; and winding the transport tape onto the unwinding spool.

2. The method according to claim 1, wherein the connecting of the ends to the corresponding tapes for splicing in the transport tape comprises butt-joining the respective end to the respective tape by means of a piece of adhesive tape.

3. The method according to claim 1, wherein the connecting of the ends to the corresponding tapes for splicing in the transport tape comprises joining the respective end to the respective tape in an overlapping manner.

4. The method according to claim 3, wherein joining in an overlapping manner comprises gluing the respective end to the respective tape together at an overlapping region by a layer of hot-melt adhesive provided on the auxiliary tape.

5. The method according to claim 1, further comprising connecting the trailer tape and the leader tape to a respective one of the unwinding spool and take-up spool by means of a material or frictional tape connection in a manner such that the trailer tape and the leader tape do not self-detach from the respective unwinding spool and take-up spool when the transport tape unit unwinds.

6. The method according to claim 5, wherein the connecting of the trailer tape and the leader tape to the respective unwinding spool and take-up spool is by means of a material tape connection comprising welding or gluing.

7. The method according to claim 6, wherein the material tape connection comprising gluing by means of a hot-melt adhesive.

8. The method according to claim 5, further comprising coating a section of at least one of the trailer tape and leader tape and the respective spool with a hot-melt adhesive, and joining the section of the trailer tape and leader tape and the respective spool in a planar fashion by applying pressure and heat by means of a welding die.

9. The method according to claim 8, further comprising applying the hot-melt adhesive in a wet form and drying the adhesive so that a portion of solids remains as the adhesive layer.

10. The method according to claim 9, wherein the adhesive layer comprises a layer thickness of between about 10 μm and about 50 μm.

11. The method according to claim 5, wherein the trailer tape and leader tape are connected to the corresponding spool over a wrap region of less than 180°.

12. The method according to claim 5, wherein the connecting of the trailer tape and the leader tape to the respective unwinding spool and take-up spool is by means of a frictional tape connection comprising a clamp connection between the trailer tape and the leader tape and the corresponding spool.

13. The method according to claim 12, wherein the tape end section is clamped in a clamping gap provided in the corresponding spool.

14. The method according to claim 1, further comprising coating the auxiliary tape with a hot-melt adhesive over its entire length by means of a coextrusion process.

15. A method for assembling a diagnostic tape unit comprising a plurality of disposable test units provided on a rollable tape such that the test units can be successively made available to a user by winding of the rollable tape, the method comprising the steps of:

integrally connecting a take-up spool and an unwinding spool of the diagnostic tape unit by an auxiliary tape, wherein no disposable test units are on the auxiliary tape, which is structured only for a tape connection of the rollable tape to the take-up and unwinding spools, and wherein the auxiliary tape has a hot-melt adhesive layer for integrally connecting the auxiliary tape to at least one of the take-up spool, the unwinding spool and a transport tape;

severing the auxiliary tape to form a leader tape extending from the take-up spool and a trailer tape extending from the unwinding spool;

connecting a leading end of the transport tape of the rollable tape including the plurality of disposable test units to the take-up spool using the leader tape extending from the take-up spool, wherein the leader tape and the transport tape are separate from one another before connecting the leading end of the transport tape to the take-up spool and are joined to one another to connect the leading end of the transport tape to the take-up spool;

connecting a trailing end of the transport tape to the unwinding spool using the trailer tape extending from the unwinding spool so that the disposable test units of the rollable tape are provided on the transport tape and no disposable test units are on the trailer tape, wherein the trailer tape and the transport tape are separate from one another before connecting the trailing end of the transport tape to the unwinding spool and are joined to one another to connect the trailing end of the transport tape to the unwinding spool; and winding the transport tape onto the unwinding spool.

16. The method according to claim 15, wherein the connecting of the ends to the corresponding tapes for splicing in the transport tape comprises butt-joining the respective end to the respective tape by means of a piece of adhesive tape.

17. The method according to claim 15, wherein the connecting of the ends to the corresponding tapes for splicing in the transport tape comprises joining the respective end to the respective tape in an overlapping manner by gluing the respective end to the respective tape together at an overlapping region by the hot-melt adhesive layer provided on the auxiliary tape.

18. The method according to claim 15, wherein the hot-melt adhesive layer of the auxiliary tape has a layer thickness of between about 10 μm and about 50 μm.

19. The method according to claim 15, wherein the leader tape is connected via the hot-melt adhesive layer to the take-up spool over a wrap region of less than 180°.

20. The method according to claim 19, wherein the wrap region is less than 90°.

21. The method according to claim 15, wherein the trailer tape is connected via the hot-melt adhesive layer to the unwinding spool over a wrap region of less than 180°.

22. The method according to claim 21, wherein the wrap region is less than 90°.

* * * * *